United States Patent
Sattler et al.

(10) Patent No.: US 6,197,964 B1
(45) Date of Patent: Mar. 6, 2001

(54) METHOD FOR THE PRODUCTION OF 2,6-DICHLORO-5-FLUORONICOTINONITRILE AND THE CHEMICAL COMPOUND 3-CYANO-2-HYDROXY-5-FLUOROPYRIDE-6-ONE-MONOSODIUM SALT ITS TAUTOMERS

(75) Inventors: Andreas Sattler, Düsseldorf; Guido Steffan, Odenthal; Bernd Griehsel, Bottrop, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/402,047
(22) PCT Filed: Mar. 19, 1998
(86) PCT No.: PCT/EP98/01617
§ 371 Date: Sep. 27, 1999
§ 102(e) Date: Sep. 27, 1999
(87) PCT Pub. No.: WO98/43958
PCT Pub. Date: Oct. 8, 1998

(30) Foreign Application Priority Data

Apr. 1, 1997 (DE) .............................. 197 13 506

(51) Int. Cl.$^7$ ...................... C07D 213/84; C07D 213/85
(52) U.S. Cl. ............................... 546/286; 546/288
(58) Field of Search .............................. 546/286

(56) References Cited

U.S. PATENT DOCUMENTS

| 4,225,716 | * | 9/1980 | Buhler et al. | ......... 546/286 |
| 5,675,012 | | 10/1997 | Ohi | ......... 546/286 |

FOREIGN PATENT DOCUMENTS

| 2307444 | 8/1974 | (DE) . |
| 0 333020 | 9/1989 | (EP) . |
| 0 700 903 | 3/1996 | (EP) . |
| 2158825 | 11/1985 | (GB) . |
| 2191776 | 12/1987 | (GB) . |

OTHER PUBLICATIONS

Chem. Pharm. Bull. , vol 35, (month unavailable) 1987, pp. 2280–2285, XP–002073588, Teruyuki Miyamoto, Hiroshi Egawa and Jun–ichi Matsumoto, Pyridonecarboxylic Acids as Antibacterial Agents, VIII. An Alternative Synthesis of Enoxacin via Fluoronicotinic Acid Derivatives.

Angew. Chem. 92 (month unavailable) 1980, p. 390, Von Werner Jünemann, Hans–Joachim Opgenorth und Horst Secheuermann, Professor Matthias Seefelder, Aminopyridine.

* cited by examiner

Primary Examiner—Alan L. Rotman
(74) Attorney, Agent, or Firm—Joseph C. Gil; Diderico van Eyl

(57) ABSTRACT

The process according to the invention can be illustrated by way of example by the following equation:

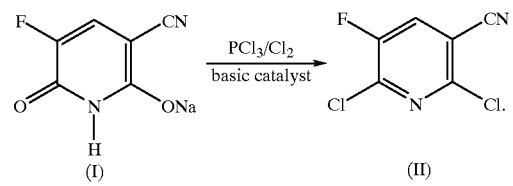

The monosodium salt of the 3-cyano-2-hydroxy-5-fluoropyrid-6-one (cf. Formula (I)) and/or tautomers thereof are preferably employed in the process according to the invention.

The use of a basic catalyst enables significantly lower amounts of chlorinating agent to be employed in the chlorination according to the invention than is necessary, for example, for chlorination of the free dihydroxy compound according to EP-A 333 020. Furthermore, the product 2,6-dichloro-5-fluoronicotinonitrile is obtained in a high purity and high yields after hydrolysis, which is not the case if the conditions according to EP-A 333 020 are applied.

Basic catalysts which can be used for the process according to the invention are, for example, organic bases, for example aliphatic and aromatic amines and amides, and also inorganic bases, for example basic compounds of nitrogen and phosphorus and salts thereof. Preferred basic catalysts are: pyridine, pyridines alkylated with 1 to 3 $C_1$–$C_6$-alkyl groups, piperidine, piperidines, imidazoles and indoles alkylated with 1 to 3 $C_1$–$C_6$-alkyl groups, N—$C_1$–$C_6$-alkylaminopyridines, N—di-$C_1$–$C_6$-alkylated anilines, tertiary N—$C_1$–$C_6$-alkylamines, urea and urea derivatives. Particularly preferred basic catalysts are triethylamine, urea and ethylpiperidine.

10 Claims, No Drawings

METHOD FOR THE PRODUCTION OF 2,6-DICHLORO-5-FLUORONICOTINONITRILE AND THE CHEMICAL COMPOUND 3-CYANO-2-HYDROXY-5-FLUOROPYRIDE-6-ONE-MONOSODIUM SALT ITS TAUTOMERS

BACKGROUND OF THE INVENTION

The present invention relates to an advantageous process for the preparation of 2,6-dichloro-5-fluoronicotinonitrile starting from 3-cyano-2-hydroxy-5-fluoropyrid-6-one and/or its tautomers and/or its salts and/or tautomers thereof, and to 3-cyano-2-hydroxy-5-fluoropyrid-6-one monosodium salt and tautomers thereof (called 3-cyano-2-hydroxy-5-fluoropyrid-6-one monosodium salt in the following).

2,6-dichloro-5-fluoronicotinonitrile is the starting compound for synthesis of important units for antibiotics from the class of so-called "aza"-analogous quinolones (cf., for example, German Offenlegungsschrift 35 14 076). Such a use also requires preparation processes for the intermediate products which give the intermediate products in a high purity, high yield and high economic efficiency.

Some preparation processes for 2,6-dichloro-5-fluoronicotinonitrile are already known. Thus, 2,6-dichloro-5-fluoronicotinonitrile can be prepared starting from 2,6-dichloro-5-fluoro-3-trichloromethylpyridine by reaction with ammonium chloride and copper oxide in sulfolane at 180 to 190° C. (cf., for example, WO 95 26 340). However, the large amount of hydrochloric acid formed and the large amounts of solid to be handled are a great disadvantage for industrial realizations.

2,6-dichloro-5-fluoronicotinonitrile can furthermore be obtained from 2,6-dihydroxy-5-fluoronicotinonitrile by reaction with phosphorus pentachloride in phosphorus oxychloride (cf., for example, EP-A 333 020). If 3-cyano-2-hydroxy-5-fluoropyrid-6-one monosodium salt, which is not yet known in the literature, is reacted under the conditions described in EP-A 333 020, the desired product is obtained in a yield of only 67% at a purity of 72.6% (cf. Example 2).

Reworking of the process described in EP-A 333 020 moreover shows a decisive disadvantage that if 2.25 equivalents of phosphorus pentachloride, based on the hydroxyl functions to be chlorinated, are used, relatively large amounts of more highly chlorinated by-products are formed, in addition to the desired product 2,6-dichloro-5-fluoronicotinonitrile.

The use of phosphorus pentachloride, which, as a solid, in large amounts, can be handled only with great difficulty and with a very high expenditure on safety, furthermore presents extreme problems, and the hydrolysis necessary for working up is made difficult due to the high residual content of phosphorus pentachloride and the production of relatively large amounts of phosphorus-containing waste waters.

For chlorination of analogous dihydroxynicotinonitriles, the sole use of phosphorus pentachloride (cf., for example, Chem. Pharm. Bull. 35 2280–2285 (1987)) is described, which presents great problems industrially for the above-mentioned reasons. For this purpose, the sole use of phosphorus oxychloride as a solvent and chlorinating agent is also described (cf., for example, German Offenlegungsschrift 23 07 444) as well as an addition of large amounts (163 mol %) of triethylamine (cf., for example, Angew. Chem. 92, 390 (1980)).

The reaction of 3-cyano-2-hydroxy-5-fluoropyrid-6-one monosodium salt exclusively with phosphorus oxychloride (as a solvent and chlorinating agent) leads to no reaction. Even at elevated temperature, phosphorus oxychloride is not sufficiently reactive. 2,6-dichloro-5-fluoronicotinonitrile is to be detected in the product isolated only in traces, and the addition of triethylamine also does not lead to a noticeable reaction. In the system of phosphorus oxychloride/triethylamine/reduced amounts of phosphorus pentachloride (1.15 equivalents per function to be chlorinated), low yields and a higher proportion of undesirable by-products are again observed (cf. Example 3).

There is therefore still a need for a process for the preparation of 2,6-dichloro-5-fluoronicotinonitrile which can readily be carried out industrially, gives the product with good yields and in good purities and is economically advantageous.

DESCRIPTION OF THE INVENTION

A process has now been found for the preparation of 2,6-dichloro-5-fluoronicotinonitrile, which comprises reacting 3-cyano-2-hydroxy-5-fluoropyrid-6-one and/or its tautomers and/or its salts and/or tautomers thereof with phosphorus trichloride and chlorine gas in a solvent with the addition of a basic catalyst at 30 to 300° C. and then hydrolyzing the product.

The process according to the invention can be illustrated by way of example by the following equation:

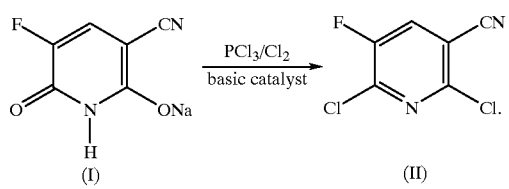

The monosodium salt of the 3-cyano-2-hydroxy-5-fluoropyrid-6-one (cf. Formula (I)) and/or tautomers thereof are preferably employed in the process according to the invention.

The use of a basic catalyst enables significantly lower amounts of chlorinating agent to be employed in the chlorination according to the invention than is necessary, for example, for chlorination of the free dihydroxy compound according to EP-A 333 020. Furthermore, the product 2,6-dichloro-5-fluoronicotinonitrile is obtained in a high purity and high yields after hydrolysis, which is not the case if the conditions according to EP-A 333 020 are applied.

Basic catalysts which can be used for the process according to the invention are, for example, organic bases, for example aliphatic and aromatic amines and amides, and also inorganic bases, for example basic compounds of nitrogen and phosphorus and salts thereof. Preferred basic catalysts are: pyridine, pyridines alkylated with 1 to 3 $C_1$–$C_6$-alkyl groups, piperidine, piperidines, imidazoles and indoles alkylated with 1 to 3 $C_1$–$C_6$-alkyl groups, N—$C_1$–$C_6$-alkylaminopyridines, N—di-$C_1$ –$C_6$-alkylated anilines, tertiary N—$C_1$–$C_6$-alkylamines, urea and urea derivatives. Particularly preferred basic catalysts are triethylamine, urea and ethylpiperidine.

A particular advantage here is that the catalyst can be employed in small amounts of, for example, 0.1 to 20 mol %, based on the substance to be chlorinated. This amount is preferably 1 to 15 mol %, particularly preferably 10 to 15 mol %. A stoichiometric addition of triethylamine, as in the preparation of the dichloro-nicotinonitrile from dihydroxy-nicotinonitrile according to the abovementioned literature reference from Angew. Chem., is not necessary according to the invention.

It is advantageous to employ the phosphorus trichloride in excess with respect to the chlorine gas and to carry out the reaction such that at least a small excess of phosphorus trichloride is always present in the reaction mixture. For example, chlorine gas can be employed in molar ratios to phosphorus trichloride of 0.1:1 to 0.99:1. This ratio is preferably 0.5:1 to 0.99:1, particularly preferably 0.9:1 to 0.99:1.

A particular advantage of the process according to the invention is that chlorine gas can be employed merely in an amount of 1 to 2 equivalents, based on each functional group to be chlorinated, instead of 2.25 equivalents of phosphorus pentachloride in the procedure analogously to EP-A 333 020. Preferably, 1.5 to 2 equivalents of chlorine gas, based on each functional group to be chlorinated, are employed.

Solvents which can be employed for carrying out the process according to the invention are, for example, phosphorus oxychloride and largely inert organic solvents, for example aromatic or aliphatic hydrocarbons, which can also be halogenated, such as tetralin, ligroin, petroleum ether, chlorobenzenes, methylene chloride or chloroform, ethers, such as diethyl ether, dibutyl ether, methyl butyl ether or tetrahydrofuran, polar aprotic solvents, such as sulfolane or N-methylpyrrolidone, or any desired mixtures thereof. Preferred solvents are phosphorus oxychloride, chloroform, methyl butyl ether, N-methylpyrrolidone and any desired mixtures thereof. Phosphorus oxychloride is preferably the sole solvent.

The solvent can be employed, for example, in amounts of 40 to 99% by weight, preferably 60 to 95% by weight, in particular 80 to 95% by weight, based on the substance to be chlorinated employed.

The chlorination is preferably carried out at temperatures between 20 and 200° C., particularly preferably between 70 and 120° C.

In a preferred embodiment of the process according to the invention, a procedure is followed in which the substance to be chlorinated is initially introduced into a stirred vessel in a solvent or solvent mixture, the catalyst and the phosphorus trichloride are added, the mixture is then heated up to the desired reaction temperature, the chlorine gas is subsequently metered in and, finally, the mixture is kept at temperatures in the range stated for the reaction temperature for some time.

The time for metering in the chlorine gas can be, for example, from 1 to 10 hours, and the time for the after-reaction can be, for example, from 1 to 20 hours.

A procedure can also be followed in which the chlorine gas is already metered in during the entire period of heating up to the desired reaction temperature or during a part thereof.

A procedure can furthermore be followed in which the substance to be chlorinated is metered in as the last component or together with the catalyst. Simultaneous metering of all the components is also possible.

When the reaction has ended, the solvent can be distilled off, together with the phosphorus oxychloride formed and excess chlorinating agent, and if appropriate employed again.

In the subsequent hydrolysis, for example, the residue present after distilling off the solvent, the phosphorus oxychloride and the excess chlorinating agent can be employed as such. It is also possible for the residue first to be taken up in a solvent. Solvents which are water-immiscible or only slightly water-miscible, for example, are used for this, for example aromatic or aliphatic hydrocarbons, which can also be halogenated, such as benzene, toluene, xylenes, tetralin, ligroin, petroleum ether, chlorobenzenes, methylene chloride or chloroform, and ethers, such as diethyl ether, dibutyl ether, methyl butyl ether or tetrahydrofuran, or any desired mixtures thereof. The residue is preferably taken up in toluene, xylenes, petroleum ether, methylene chloride, chloroform, diethyl ether, methyl butyl ether or mixtures thereof, and methylene chloride is particularly preferably used as the sole solvent in which the residue is taken up.

The hydrolysis is in general carried out with water in excess. For example, 0.5 to 2 parts by volume of water can be employed per part by volume of substance to be hydrolyzed or solution thereof. The temperature during the hydrolysis can be, for example, in the range from 0 to 100° C. If solvents which boil below 100° C. under normal pressure are present, the hydrolysis is carried out, for example, at temperatures between 0° C. and the boiling point of the solvent (under normal pressure). The hydrolysis is preferably carried out at temperatures in the range from 0 to 70° C. It is advantageous, for example, to subsequently stir the mixture at the temperatures stated for a further 1 to 2 hours. If the hydrolysis has been carried out in the absence of a solvent, it is advantageous to add a solvent of the type mentioned after the hydrolysis.

A solution of 2,6-dichloro-5-fluoronicotinonitrile which can be further processed directly, can be obtained by phase separation. If desired, 2,6-dichloro-5-fluoronicotinonitrile can be isolated from the solution, for example by evaporation, in a high yield and high purity.

Summarizing, the process according to the invention has a number of advantages. It gives 2,6-dichloro-5-fluoronicotinonitrile in high purities and good yields, it manages without solid chlorinating agents, and it requires smaller amounts of chlorinating agent than processes according to the prior art and bases only in catalytic amounts. Furthermore, practically no more highly chlorinated products are formed, and the amount of phosphorus-containing waste waters obtained is reduced.

The 3-cyano-2-hydroxy-5-fluoropyrid-6-one monosodium salt, which is preferred as the starting substance, and its tautomers have not been previously described in the literature. The present invention therefore also relates to them. 3-cyano-2-hydroxy-5-fluoropyrid-6-one monosodium salt and its tautomers can be obtained, for example, by reacting 3-cyano-2-hydroxy-5-fluoropyrid-6-one, which is known, and/or its tautomers with a $C_1$–$C_6$-alkyl-alcoholate, preferably an alkali metal $C_1$–$C_6$-alkyl-alcoholate, particularly preferably sodium methylate, in a mixture of an aromatic solvent, preferably toluene, and a $C_1$–$C_6$-alkyl alcohol, preferably methanol, precipitating out the salt thus formed, and/or its tautomers using a medium-strength acid, preferably acetic acid, and filtering off with suction and drying the product.

The invention is further described in the following illustrative examples in which all parts and percentages are by weight unless otherwise indicated.

EXAMPLES

3-Cyano-2-hydroxy-5-fluoropyrid-6-one was in each case employed in the form of a tautomer mixture predominantly comprising this tautomer.

Example 1

240 g of 3-cyano-2-hydroxy-5-fluoropyrid-6-one monosodium salt (cf. Example 8) were initially introduced into 2,400 g of phosphorus oxychloride. 15.8 g of triethylamine and subsequently 648 g of phosphorus trichloride were then added while heeding the evolution of heat. The mixture was heated to the reflux temperature (74° C., evolution of hydrogen chloride) and 312 g of chlorine were then passed in over a period of 2 hours, the reflux temperature slowly rising to 106° C. and a vigorous evolution of hydrogen chloride being observed. To bring the reaction to completion, after the chlorine had been passed in, the mixture was heated under reflux for a further 8 hours. Thereafter, 2794 g of phosphorus oxychloride (comprising excess phosphorus trichloride) were distilled off at a bottom temperature of about 70° C., the pressure slowly being reduced down to 120 mbar. The mixture was allowed to cool and the residue was taken up in methylene chloride. The suspension formed was added slowly to water, while heeding the evolution of heat, during which the temperature rose up to 40° C. (reflux of methylene chloride). The mixture was then subsequently stirred at 40° C. for 1 hour and allowed to cool, the organic phase was separated off and the aqueous phase was extracted with fresh methylene chloride. The combined methylene chloride phases were dried and evaporated on a rotary evaporator. The residue which remained was dried in vacuo at 60° C. 232.5 g of 2,6-dichloro-5-fluoronicotinonitrile (purity 94.7%, yield 85% of theory) were obtained as a brown-yellow solid.

Example 2

(For comparison, reworking of EP-A 3 330 020)

182 g of phosphorus pentachloride were initially introduced slowly into 300 g of phosphorus oxychloride. 30 g of 3-cyano-2-hydroxy-5-fluoropyrid-6-one monosodium salt were then added. The mixture was heated to the reflux temperature (114° C., evolution of hydrogen chloride) and stirred at this temperature for a further 20 hours. Thereafter, the phosphorus oxychloride was distilled off in vacuo. The residue was allowed to cool and was taken up in methylene chloride. The suspension formed was then added slowly to ice-water. After separation of the phases, the organic phase was separated off, dried and evaporated on a rotary evaporator. The residue which remained was dried in vacuo at 60° C. 30.3 g of a brown solid which consisted of 2,6-dichloro-5-fluoronicotinonitrile to the extent of 72.6% by weight (yield 67% of theory), a nicotinonitrile containing three chlorine atoms (GC/MS) to the extent of 19.2% by weight and four other, in some cases highly chlorinated compounds to the extent of about 8% by weight in total were obtained.

Example 3

(For comparison, use of phosphorus oxychloride with/without triethylamine and a reduced amount of phosphorus pentachloride).

30 g of 3-cyano-2-hydroxy-5-fluoropyrid-6-one monosodium salt were initially introduced slowly into 300 g of phosphorus oxychloride and the mixture was heated to the reflux temperature (106° C.) and stirred at this temperature for 2 hours. Up to this point in time, no evolution of hydrogen chloride at all was to be observed (negative conversion control).

After cooling, 2.0 g of triethylamine were then cautiously (exothermic) added. The mixture was heated again to the reflux temperature (106° C.) and stirred at this temperature for a further 2 hours. Up to this point in time also, no evolution of hydrogen chloride at all was to be observed (negative conversion control).

81.2 g of phosphorus pentachloride were then added at room temperature and the mixture was then heated under reflux (112° C.) for 20 hours. Within the first hours, moderate evolution of hydrogen chloride was observed here. Thereafter, the phosphorus oxychloride was distilled off in vacuo. The mixture was allowed to cool and the residue was taken up in methylene chloride. The suspension which had formed was then poured slowly onto ice-water. The organic phase was separated off and the aqueous phase was extracted once more with fresh methylene chloride. The combined methylene chloride phases were dried and evaporated on a rotary evaporator. The residue which remained was dried in vacuo at 60° C. 27.0 g of a brown solid which consisted of 2,6-dichloro-5-fluoronicotinonitrile to the extent of 83.1% by weight (yield 60% of theory) and further unknown compounds to the extent of about 15% by weight in total were obtained. Traces of unreacted educt (0.02% by weight) were furthermore found.

Example 4

240 g of 3-cyano-2-hydroxy-5-fluoropyrid-6-one monosodium salt were reacted analogously to Example 1, but the hydrolysis was carried out at room temperature. 227.6 g of 2,6-dichloro-5-fluoronicotinonitrile (purity 84.7% by weight, yield 74% of theory) were obtained as a brown-yellow solid.

Example 5

48 g of 3-cyano-2-hydroxy-5-fluoropyrid-6-one monosodium salt were reacted analogously to Example 1, but with 1.9 g of urea as the catalyst instead of triethylamine.

48 g of 2,6-dichloro-5-fluoronicotinonitrile (purity 88.5% by weight, yield 81.5% of theory) were obtained as a brown-yellow solid.

Example 6

48 g of 3-cyano-2-hydroxy-5-fluoropyrid-6-one monosodium salt were reacted analogously to Example 1, but with 3.5 g of ethyl piperidine as the catalyst instead of triethylamine.

46 g of 2,6-dichloro-5-fluoronicotinonitrile (purity 92.2% by weight, yield 81.5% of theory) were obtained as a brown-yellow solid.

Example 7

168 g of 3-cyano-2-hydroxy-5-fluoropyrid-6-one monosodium salt were reacted analogously to Example 1, but the metering in of chlorine gas was carried out in parallel with the heating up from room temperature to 73° C. over a period of 2 hours. After a further 4 hours, the reflux temperature was reached and the mixture was then stirred at this temperature for a further 6 hours.

176.5 g of 2,6-dichloro-5-fluoronicotinonitrile (purity 93.9% by weight, yield 90.9% of theory) were obtained as a brown-yellow solid.

Example 8

(Synthesis of 3-cyano-2-hydroxy-5-fluoropyrid-6-one monosodium salt)

154.1 g of 3-cyano-2-hydroxy-5-fluoropyrid-6-one dissolved in 300 ml of toluene, were added dropwise to 77 g of sodium methylate in 250 ml of methanol, while cooling at 5° C. The reaction mixture was then allowed to warm to room temperature and was stirred at this temperature for a further hour. 200 g of glacial acetic acid and then 200 ml of water were subsequently added, while cooling at 5° C. The solid which had precipitated out was filtered off with suction and washed with a little cold toluene. After drying, 165.5 g of 3-cyano-2-hydroxy-5-fluoropyrid-6-one monosodium salt (yield 94%) were obtained.

| $^1$H-NMR (D$_6$-DMSO): δ[ppm] = | 2.5 (s, —OH, 1H, partly exchanged), 7.1 (d, $^3$JH$_{HF}$~ 21 Hz, Ar—H, 1H), |
|---|---|
| $^{13}$C-NMR (D$_6$-DMSO): δ[ppm] = | 67.8 (d, $^3$J$_{CF}$~ 7.3 Hz, —$\underline{C}$H(CN)—), 121.2 (s, —$\underline{C}$N), 125.8 (d, $^2$J$_{CF}$~ 18.4 Hz, —CF=$\underline{C}$H—C(CN)H—), 137.9 (d, $^1$J$_{CF}$~ 218.8 Hz, —$\underline{C}$F=), 157.8 (d, $^2$J$_{CF}$~ 25.7 Hz, —O—$\underline{C}$(=N)—CF), 163.4 (s, $\underline{C}$=O). |
| Elemental analysis: | C   H   N |
| calculated: | 40.9%   1.15%   15.9% |
| found: | 40.3%   1.30%   15.7% |
| Atomic absorption spectroscopy for fluorine | calculated F = 10.8%   found F = 10.5% |
| Melting point: | non-uniform, decomposition |
| Colour: | brown-beige amorphous solid |

The spectroscopic data show that the tautomer mixture obtained comprises predominantly 3-cyano-2-hydroxy-5-fluoropyrid-6-one monosodium salt.

Although the present invention has been described in detail with reference to certain preferred versions thereof, other variations are possible. Therefore, the spirit and scope of the appended claims should not be limited to the description of the versions contained therein.

What is claimed is:

1. A process for the preparation of 2,6-dichloro-5-fluoronicotinonitrile which comprises reacting a reactant component selected from the group consisting of 3-cyano-2-hydroxy-5-fluoropyrid-6-one, tautomers of 3-cyano-2-hydroxy-5-fluoropyrid-6-one, salts of 3-cyano-2-hydroxy-5-fluoropyrid-6-one, and tautomers of 3-cyano-2-hydroxy-5-fluoropyrid-6-one monosodium salts with phosphorus trichloride and chlorine gas in a solvent, adding a basic catalyst at 30–300° C. and then hydrolyzing the product.

2. A composition comprising a member selected from the group consisting of the chemical compound 3-cyano-2-hydroxy-5-fluoropyrid-6-one monosodium salt and tautomers of 3-cyano-2-hydroxy-5-fluoropyrid-6-one monosodium salts.

3. The process as claimed in claim 1, wherein the basic catalyst used in the process comprises a member selected from the group consisting of aliphatic amines, aromatic amines amides basic compounds of nitrogen, basic compounds of phosphorus, salts of basic nitrogen compounds, and salts of basic phosphorous compounds.

4. The process as claimed in claim 1, wherein the catalyst is employed in an amount of 0.1 to 20 mol %, based on the reactant component.

5. The process as claimed in claim 1, wherein chlorine gas is employed in a molar ratio to phosphorus trichloride of 0.1:1 to 0.99:1.

6. The process as claimed in claim 1, wherein the chlorine gas is employed in an amount of 1 to 2 equivalents, based on each functional group to be chlorinated.

7. The process as claimed in claim 1, wherein the solvent used comprises a member selected from the group consisting of phosphorus oxychloride, aromatic hydrocarbons, aliphatic hydrocarbons, halogenated aromatic hydrocabons, halogenated aliphatic hydrocarbons, ethers polar aprotic solvents, and mixtures thereof.

8. The process as claimed in claim 1, wherein the chlorination is carried out at 20 to 200° C.

9. The process as claimed in claim 1, wherein, when the reaction has ended, the solvent is distilled off together with the phosphorus oxychloride formed and excess chlorinating agent, a solvent is added to the residue which remains, if appropriate, and the hydrolysis is carried out at 0 to 100° C. with water in excess.

10. The process as claimed in claim 1, wherein, after the hydrolysis, the mixture is subsequently stirred at 0 to 100° C. for a further 1 to 2 hours.

* * * * *